United States Patent
Lobsiger et al.

[11] Patent Number: 6,119,630
[45] Date of Patent: Sep. 19, 2000

[54] INSTALLATION FOR IN SITU MONITORING THE QUALITY OF HABITAT OF AQUATIC ORGANISMS

[75] Inventors: Ulrich Lobsiger, Halifax; Joan L. Manuel, Lantz, both of Canada

[73] Assignee: 3042015 Nova Scotia Limited, Halifax, Canada

[21] Appl. No.: 09/082,599

[22] Filed: May 21, 1998

[30] Foreign Application Priority Data

May 26, 1997 [CA] Canada ................................. 2206103

[51] Int. Cl.7 ............................................. A01K 61/00
[52] U.S. Cl. ............................................. 119/238; 119/421
[58] Field of Search ................................. 119/238, 239, 119/240, 421; 340/850; 390/25, 26, 27, 28, 29

[56] References Cited

U.S. PATENT DOCUMENTS

| | | |
|---|---|---|
| 3,017,817 | 1/1962 | Sampson . |
| 3,261,274 | 7/1966 | Smith . |
| 3,324,239 | 6/1967 | Jacobson . |
| 3,738,248 | 6/1973 | Fish et al. . |
| 3,750,547 | 8/1973 | Walthier et al. .......................... 396/25 |
| 4,626,992 | 12/1986 | Greaves et al. . |
| 4,723,511 | 2/1988 | Solman et al. . |
| 4,744,331 | 5/1988 | Whiffin . |
| 4,888,703 | 12/1989 | Baba et al. . |
| 5,140,855 | 8/1992 | Gruber . |
| 5,222,458 | 6/1993 | Pippy . |
| 5,469,144 | 11/1995 | Gradzki et al. . |

FOREIGN PATENT DOCUMENTS 2186001 9/1995 Canada .

*Primary Examiner*—Peter M. Poon
*Assistant Examiner*—Yvonne R. Abbott
*Attorney, Agent, or Firm*—Mario D. Theriault

[57] ABSTRACT

An installation for in situ monitoring the quality of a habitat of aquatic organisms with minimal disturbance to the aquatic organisms. In a first aspect of the present invention, the monitoring installation uses invertebrate sentinel species such as mussels, clams, oysters and scallops. The monitoring installation comprises broadly, a buoy; a mooring and a monitoring apparatus comprising; a framework having an upper end connected to the buoy and a lower end connected to the mooring. There is also provided a camera attached to the framework. The camera is adapted for underwater operation and has image data generating and transmitting capabilities for transmitting a number of images to a remote receiver. A support structure is detachably mounted to the framework and has rotary retainers for movably supporting one or more socks of mollusks in front of the camera.

20 Claims, 6 Drawing Sheets

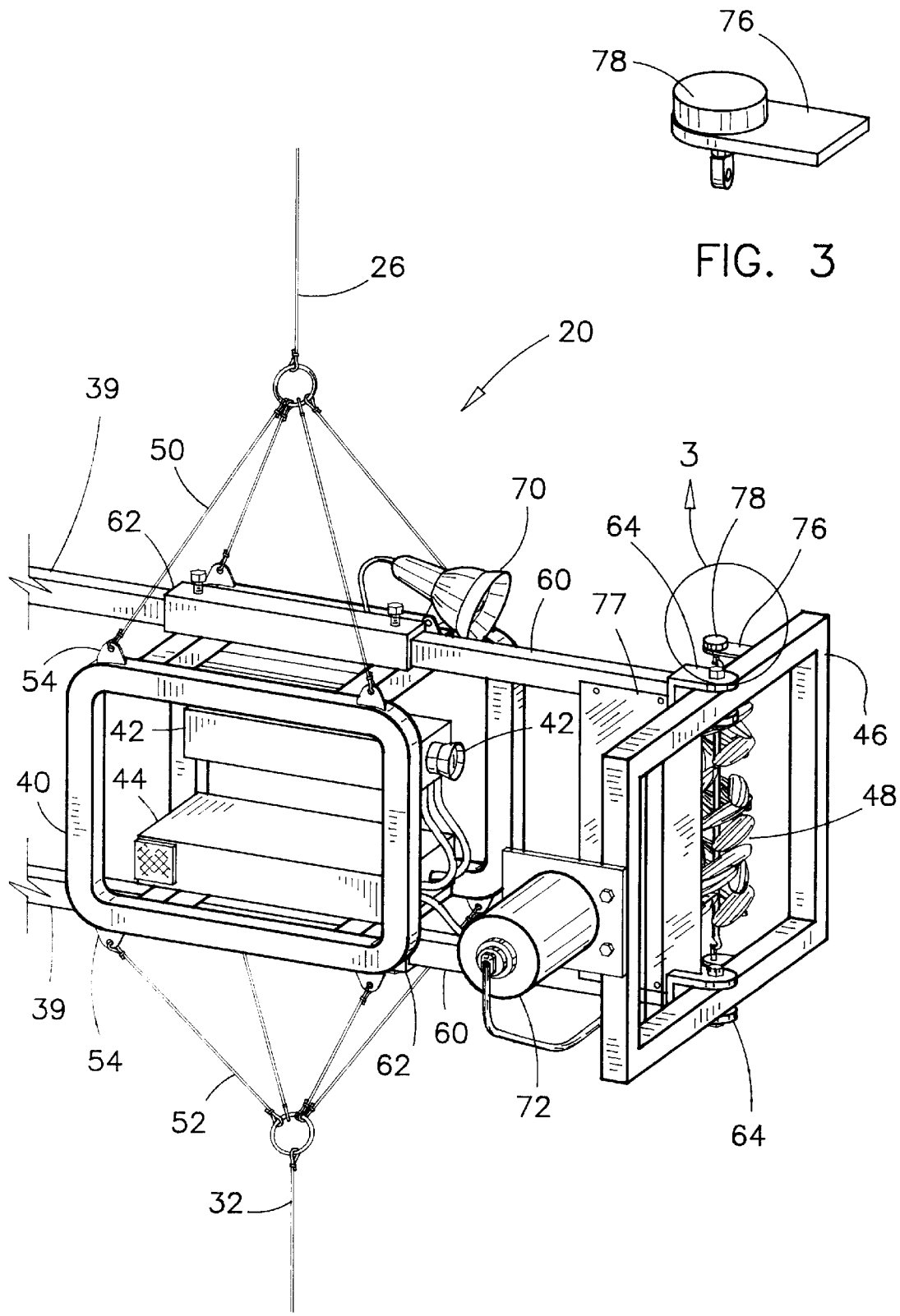

INSTALLATION FOR IN SITU MONITORING THE QUALITY OF HABITAT OF AQUATIC ORGANISMS

FIELD OF THE INVENTION

The present invention relates to early warning systems for monitoring coastal water quality, and more particularly, it relates to a portable submersible apparatus for in situ monitoring the quality of habitat of aquatic organisms, or for in situ detecting lethal and sublethal pollution in inland or sea water.

BACKGROUND OF THE INVENTION

A good understanding of the coastal ecosystems and the monitoring of water quality have become essential to the success of any aquaculture program. Therefore, in recent years there have been several proposals developed for monitoring the quality of water at fish rearing installations and around natural shellfish habitats to ensure a healthy condition of the cultivated species.

Although these systems were developed primarily for the aquaculture industry, other applications include: the provision for an early warning of the onset of toxic bloom events that affect seafood crops designated for human consumption; the detection of pollution at point-source discharges around industrial operations such as pulp & paper; and the detection of pollution and sediment re-suspension during offshore oil & gas operations and marine construction projects.

In a first example of the prior art systems, the U.S. Pat. No. 4,626,992, issued on Dec. 2, 1986 to J. Greaves; R. S. Wilson; and E. H. Smith, discloses a water quality early warning system wherein aquatic organisms are placed in monitoring tanks and are exposed to the water from a selected source. These organisms are observed by cameras. A computer and software are used for analysing the organisms' movements and for comparing the observed movements with the set of prediction parameters. When the organisms' observed movements do not correspond to the predicted parameters, a warning message is generated. Other apparatus for monitoring the behaviour of fish in a fish tank using a camera and an image analysis software are also disclosed in U.S. Pat. No. 4,888,703 issued on Dec. 19, 1989 to K. Baba et al., and in U.S. Pat. No. 5,222,458 issued on Jun. 29, 1993 to J. H. C. Pippy.

Another example of the water quality monitoring systems of the prior art using a fish tank is described in the U.S. Pat. No. 4,723,511, issued on Feb. 9, 1988 to A. J. Solman and G. P. Evans. In the described system, the behaviour of fish is monitored by measuring the voltage from a pair of electrodes mounted in the fish tank in which water to be monitored is circulated. This system monitors a small oscillating voltage which is produced by the fish in ventilation. A rise in ventilation frequency or an increase in the frequency of abnormal behaviour such as coughing is indicative of the contaminated water.

In that respect, a method and a processor for interpreting the ventilation frequency of fish and for generating an alarm when the ventilation frequency reaches a threshold value is disclosed in U.S. Pat. No. 5,469,144, issued on Nov. 21, 1995 to P. Gradzki, M. Kaynor, and D. Gruber.

A further system for monitoring the quality of water in situ is disclosed in U.S. Pat. No. 4,744,331, issued on May 17, 1988 to D. E. Whiffin. The system uses cameras mounted in a sea pen for monitoring the weight gain and diseases in fish retained in the sea pen. The cameras in this installation are controllable from a remote location, by an operator using a monitor screen and a control panel.

Most water quality monitoring systems of the prior art rely on the behaviour of fish confined in a fish tank or in a floating enclosure. In the case of the fish tank systems, the monitoring of water quality relies on discrete field sampling followed by laboratory analysis. In the case of the fish pen installation, the equipment is complex, expensive and the image analyses are better interpreted by marine biologists. Furthermore, the fish specimens in both cases are monitored while moving about in a restrained mode, and therefore, a certain deviation factor must be considered when defining a normal behaviour.

Therefore, it is believed that there is still an important market demand for a portable monitoring apparatus, which is reliable, relatively inexpensive, which can be transported and deployed using a small boat; which can be interpreted by a fish farmer having little knowledge of an aquatic organism behaviour when the organism is under stress, and most importantly, which can be used for monitoring in situ, one or more aquatic organisms in a true natural environment.

SUMMARY OF THE INVENTION

In the present invention, however, there is provided an installation for in situ monitoring the quality of a habitat of aquatic organisms with minimal disturbance to the aquatic organisms. In a first aspect of the present invention, the installation of the present invention uses invertebrate sentinel species such as mussels, clams and scallops. These species are somewhat passive animals and are easily observable. Furthermore it has been found that bivalve behaviour reliably reflects water quality. Individual or a sock of bivalves are suspended on a substrate that mimics their natural habitat. They are allowed to settle along the sock with their byssus threads, and no sensors are mounted to their shells. The bivalves may also be attached with glue or ear-hung on ropes or nylon strips.

The installation of the present invention comprises broadly, a buoy, a mooring and a portable monitoring apparatus comprising: a framework having an upper end connected to the buoy and a lower end connected to the mooring. There is also provided a camera attached to the framework. The camera is adapted for underwater operation and has data storage capabilities for registering a number of images. An instrument enclosure is also attached to the framework, and contains a variety of instruments relative to characteristics of the body of water, and a power supply battery for operating the instruments during a nominal test period. The monitoring apparatus further has a support structure mounted on the framework and extending in front of the camera. The support structure comprises rotary retainers retaining the aquatic organism specimen in front of the camera.

The installation of the present invention can be deployed in the form of an inexpensive mooring in situ, such that the test animals are in their natural environment. The specimens are monitored by the underwater camera, and both normal and stressed behaviour patterns are established and recorded. For example, the behavioural factors observed on bivalve specimens generally include various filtering modes, that is: a bivalve which is not pumping; open but not feeding; feeding; or severely stressed.

Other behavioural indicators generally considered to determine behavioural indices include events such as the number of clapping of the valves together to clear irritants particles from the mantle cavity per hour; the amount of faeces/pseudo faeces produced, or the amount of moving about to get into a better position. By observing several specimens, it is possible to determine the period of time each bivalve spends in each activity, as well as the response of the specimens to particular events. Deviations from normal behaviour caused by environmental stressors are compared with predefined alarm-thresholds values.

The principal advantage of the installation of the present invention is found in its ability to observe in situ a submarine region, to observe the behaviour of invertebrate specimens and to register certain observations related to the comportment of these specimens. The recorded data can then be analysed and combined to determine one or more denominate mathematical factors hereinafter referred to as the behavioural, or 'activity' indices of the invertebrate specimens in this submarine region. These indices are a direct indicative of the quality of water in this submarine region.

In another aspect of the installation of the present invention, there are also provided a first light mounted to the framework of the monitoring apparatus, and which is oriented to emit light toward the aquatic organism specimen for lighting the aquatic organism specimen during an operation of the camera; and a second light mounted to the support structure and oriented to emit light in a direction perpendicular to a line of sight of the camera. The operation of the second light causes reflections on suspended particles near the aquatic organism specimen, and causes the particles to become visible to the camera. Hence, the monitoring apparatus of the installation of the present invention is a single instrument package capable of recording both the floc dynamics of a submarine region and/or the behaviour of invertebrate species such as mollusks, exposed to the conditions of that region.

Other functions of the monitoring apparatus of the installation of the present invention includes the ability to measure and record several marine life supporting characteristics of the aquatic site. The variation in current speed over the tidal cycle is known to change the settling of sedimentation on the site, to bring in particles of nutrients from different parts of a bay (e.g. on-shore or off-shore) or to re-suspend particles from the bottom. Therefore, the measurement of marine snow, amorphous macro-aggregates suspended in seawater, combined with the measurement of physical parameters such as tidal current, salinity and temperature, are provided by the instrumentation of the monitoring apparatus, for recording valuable data which are directly related to the compatibility of a site with the culture of aquatic species for example.

Although the installation of the present invention is advantageously usable as an aquaculture management tool, it is also useful for detecting pollution in a body of water. It is known by marine life scientists that fish and other aquatic animals are very sensitive to pollution and are often used as bio-sensors for detecting quantities of pollutants which are too dilute for conventional testing. Therefore, sublethal environmental effects on invertebrates can be monitored with the installation of the present invention by observing the behaviour of the animals over a relatively short period of time (days), without having to examine time-consuming effects such as growth rate of the shell or soft body tissue. It is thereby possible to observe specimens of one or several species, to detect stressful conditions at a given site or to detect capacity problems before growth has been stunted. For pollution monitoring, several individuals from more than one species, a mixed collection of mollusks containing more and less sensitive species for example, are placed in the field of view of the camera of the apparatus of the present invention, such as the old-time method of nurturing a canary in coal mine for detecting toxic gases, to detect pollution at levels which are sublethal to humans. Hence, the observation of the invertebrate specimens provides an integrated synopsis of the overall quality of an aquatic environment.

In this respect, and according with another aspect of the installation of the present invention, the camera of the monitoring apparatus is adapted to generate digital images and the buoy contains data transmitting equipment for transmitting the digital images of the camera to a remote location. A number of installations deployed at key locations and all transmitting data in a real-time mode to a common control station is a reliable early warning system for monitoring pollution in a body of water.

BRIEF DESCRIPTION OF THE DRAWINGS

The preferred embodiments of the present invention will be further understood from the following description, with reference to the drawings in which:

FIG. 2 is a partial close-up view of the monitoring apparatus of the installation of the first preferred embodiment;

FIG. 3 is a close-up view of a rotary retainer for adjustably retaining a sock of mollusk to the monitoring apparatus, as seen in detail circle 3 in FIG. 2.

DETAILED DESCRIPTION OF THE PREFERRED EMBODIMENT

Figure 1:
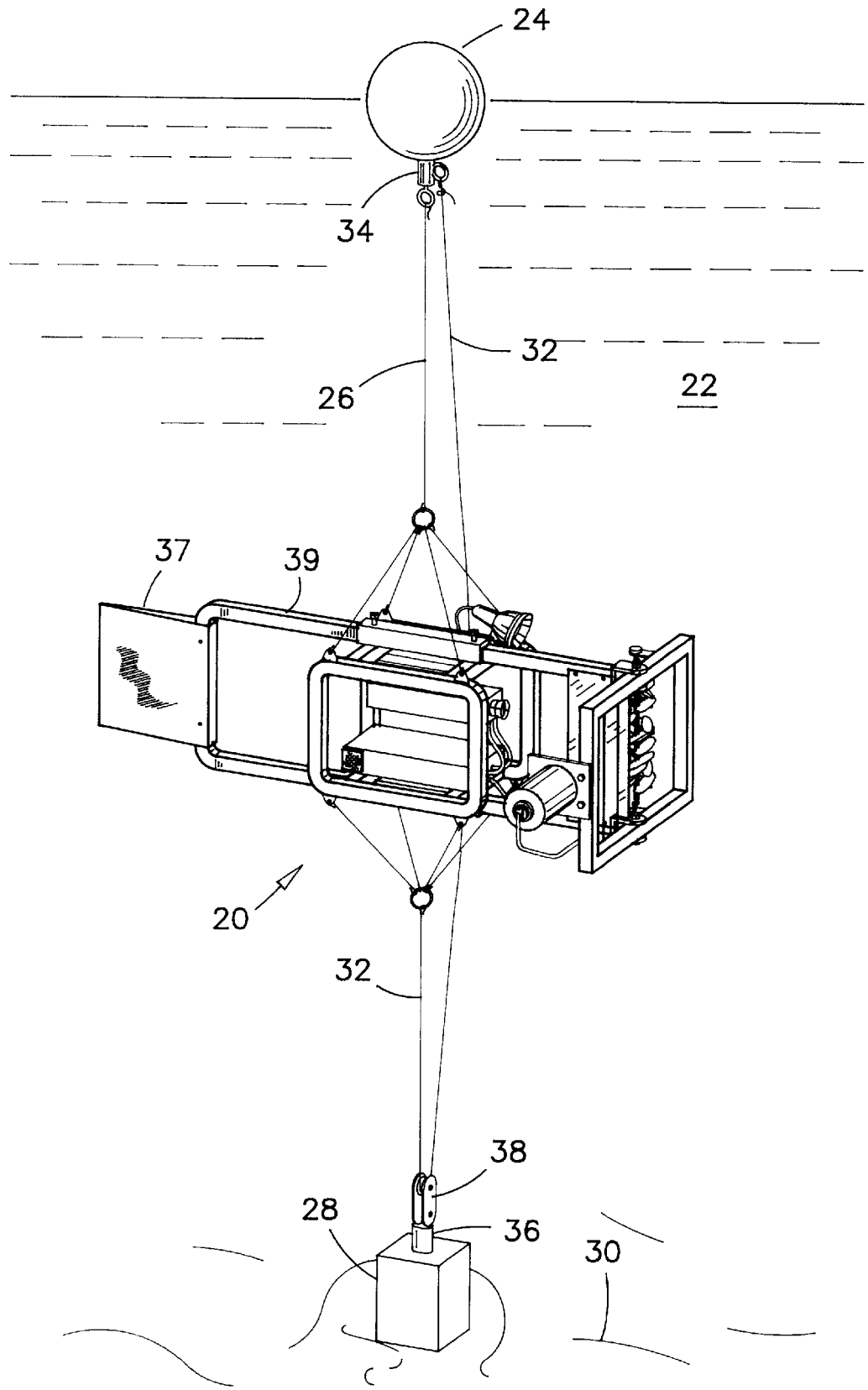
FIG. 1 illustrates the installation of a first preferred embodiment.

A monitoring installation of a first preferred embodiment is illustrated in FIG. 1. The monitoring installation comprises a monitoring apparatus 20 which is suspended in a body of water 22 to be monitored. The apparatus 20 is suspended by means of a buoy 24, buoy rope 26, a mooring 28 resting on the bottom 30 of the body of water and a mooring rope 32. The buoy 24 and the mooring 28 each has a swivel joint 34, 36 respectively for preventing tangling of the ropes from the effect of waves and current on the buoy 24 and on the apparatus 20.

The monitoring apparatus 20 of the installation of the first preferred embodiment may be deployed at any depth in the body of water 22 by adjusting the length of the buoy rope 26. When the monitoring apparatus 20 is submerged at a preferred depth, the mooring rope 32 is then pulled tight through a block pulley 38 on the mooring swivel 36 and attached to the buoy 24 for retaining the monitoring apparatus 20 at the preferred depth.

The monitoring apparatus 20 of the installation of the first preferred embodiment also has a rudder 37 attached to a rudder frame 39 extending behind the monitoring apparatus, for keeping the monitoring apparatus 20 in alignment with the currents present at the test site.

Referring now to FIGS. 2–5, the monitoring apparatus 20 of the installation of the first preferred embodiment comprises essentially a framework 40 enclosing a camera 42 and an instrumentation 44 containing a battery and various instruments for monitoring the characteristics of the submarine habitat to be evaluated. The nature of these instruments will be explained in greater details in the following pages of this disclosure and especially when making reference to FIG. 6.

Although the framework 40 of the apparatus 20 is illustrated as having has a cubical shape, it will be appreciated that an oblong or cylindrical framework is also considered within the scope of the present invention, and the shape depends solely upon the preference of the manufacturer of the apparatus.

The preferred camera 42 mounted in the framework 40 of the apparatus of the first preferred embodiment is a self-contained, battery powered and water-resistant camera having image storage capability and battery power for operations during 48-hour or longer periods. A camcorder-type camera having means for controlling an intermittent operation thereof is quite appropriate for discreetly monitoring the behaviour of mollusks. The lens on the camera 42 is preferably a wide angle marine-type lens having a refractive index suitable for use in water.

Typical underwater camera units for this application are: camcorders Hi-8 units, such as Sony TR 555™ or equivalent; or digital camcorders, such as Sony DCR-VX 1000™, or Canon Optura™. The camera is preferably mounted in a pressure resistant housing having a viewing window made of acrylic, polycarbonate, optical quality glass or the like.

The apparatus 20 of the installation of the first preferred embodiment also comprises a structure 46 extending from the framework 40 and being disposed in front of the camera 42. The structure 46 is used for supporting a representative sample of aquatic organisms in the submarine site to be evaluated. The preferred representative sample of aquatic organisms are bivalves 48, such as a sock of mussels, ear-hung scallops or other mollusks of the like, or bivalves placed in a fixed position on a frame.

The framework 40 of the apparatus 20 of the installation of the first preferred embodiment is affixed to the buoy rope 26 by a first set of stabilizing ropes 50 and to the mooring rope 32 by a second set of stabilizing ropes 52. Both sets of stabilizing ropes 50,52 are attached to eyed tabs 54 on the upper and lower outside corners of the framework 40 respectively. The length of each stabilizing rope is preferably adjusted such that the buoy rope 26 and mooring rope 32 are aligned with the centre of gravity of the apparatus 20 and the apparatus 20 is suspended horizontally. It will be appreciated that several diving weights may also be attached to the framework 40 to counterbalance the weight of the mollusks 48 and supporting structure 46, for maintaining the apparatus 20 in a horizontal alignment.

The sock support structure 46 of the apparatus 20 is pivotally supported on a pair of arms 60. The arms 60 are telescopically mounted into a pair of tubular sockets 62, one on the upper portion of the framework 40 and the other being on the lower portion of the framework 40. The arms 60 are thereby extensible and retractable relative to the camera 42 for obtaining an ideal focal distance between the sock of mollusks 48 and the lens of the camera 42.

Each arm 60 has a clevis joint 64 connected to the sock support structure 46. The plane of the structure 46 can thereby be tilted from side to side about the vertical axis of both devises 64, to vary the angle of the structure 46 relative to the line of sight of the camera 42. This articulation is particularly advantageous for varying the perspective view of the images to be generated by the camera 42.

Another important advantage of the mounting devises 64 is that the sock support structure 46 is detachable from the devises 64 and from the monitoring apparatus 20. This feature is particularly advantageous for growing various test specimens in a remote location under controlled conditions for example, on a number of support structures 46, and for carrying and mounting one of these support structures 46 to the monitoring apparatus when needed and with a specific test specimen 48 having some affinity for a site to be monitored.

The support structure 46 is preferably rectangular in shape having a height of about 16 inches (40 cm) and a length of about 24 inches (60 cm). The support structure 46 is thereby easily manipulated from the remote growing site to the test site by one person, and easily installed on the monitoring apparatus 20 with minimum disturbance to the test specimens.

The apparatus 20 of the installation of the first preferred embodiment also has a first light 70 for illuminating the sock of mollusks 48 during the operation of the camera 42. A second light 72 is also provided for illuminating marine snow in the vicinity of the sock of mollusks 48. The first light 70 is generally oriented to illuminate a region on the sock of mollusks 48 corresponding to the scope of view of the camera 42. On the monitoring apparatus of the installation of the first preferred embodiment the length of the arms 60 and the height of the structure 46 are about 12–16 inches (30–40 cm). The first light 70 is set at an angle of about 45° with the sock of mollusks 48 in order to provide an ideal illumination. The first light 70 operates simultaneously with the camera 42 for observing the behaviour of the mollusks 48.

It has been found that red light disturbs the mollusk specimens the least. For this reason, the first light 70 preferably has a tinted lens or other means for emitting red light.

The second light 72 is preferably mounted to the sock support structure 46 and is oriented transversally to the sock of mollusks 48. The second light 72 has a Fresnel lens for generating a collimated beam of light having known cross-section dimensions. The second light 72 also operates simultaneously with the camera 42 for creating reflections on suspended particles near the sock of mollusks 48, and causing these particles to become visible on the images taken by the camera 42.

Figure 4:
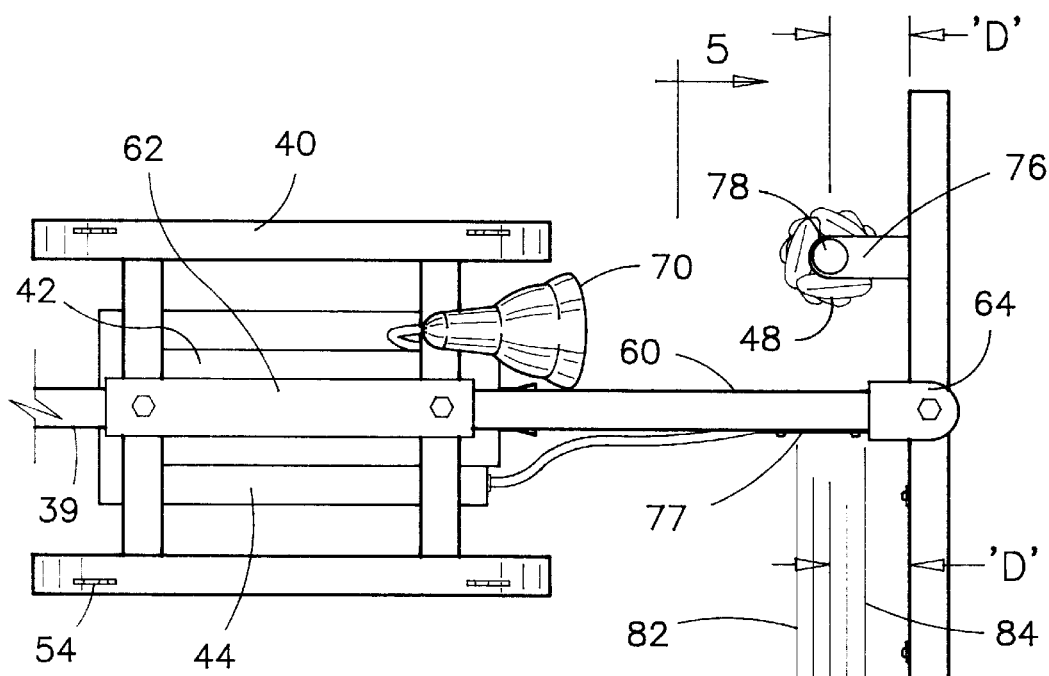
FIG. 4 is a partial top view of the monitoring apparatus of the installation of the first preferred embodiment.
Figure 5:
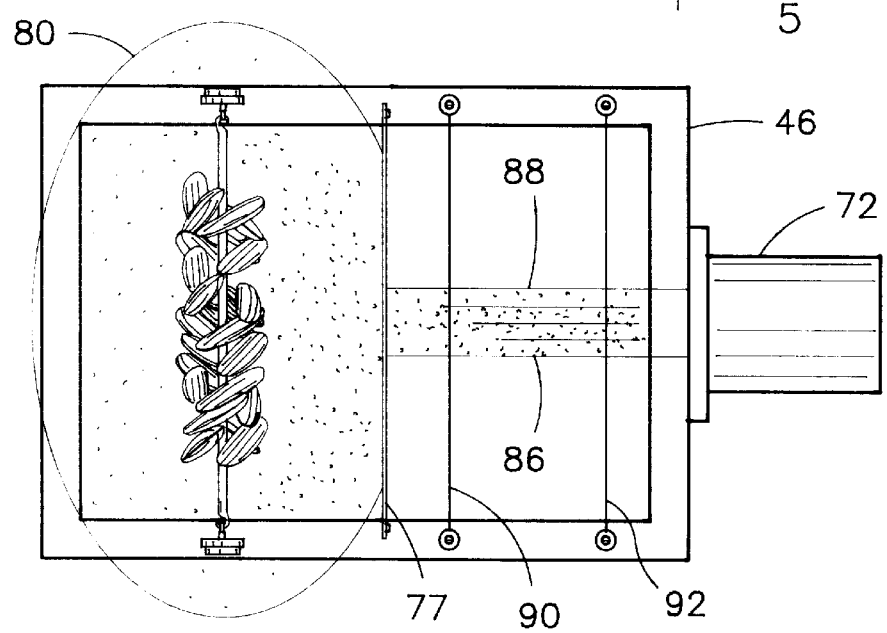
FIG. 5 illustrates a view of the mollusk specimens as seen through the camera of the monitoring apparatus of the installation of the first preferred embodiment.

Referring now particularly to FIGS. 2, 4 and 5, the second light 72 is mounted on the front side of the support structure 46 and the light beam thereof is oriented toward a front region of the structure 46. The sock of mollusks 48 is attached to mounting brackets 76 on the front side of the support structure 46, at a distance 'D' from the support structure 46 such that its position is aligned with the collimated light beam of the second light 72. The mollusks are thereby at a same focal distance from the camera 42 as the particles illuminated by the second light 72.

A baffle plate 77 is affixed to and between both telescoping arms 60 and extends between the sock of mollusks 48 and the second light 72 for blocking the light beam of the second light 72, and preventing areas of great light intensity on the mollusk specimens 48, which could adversely disturb the mollusks or affect the quality of the images taken by the camera 42.

The mounting brackets 76 further comprises a pair of rotary retainers 78 that are adjustable angularly about the axis of the sock. The sock of mollusks 48 is thereby adjustable relative to the support structure 46 so that a greatest number of specimens are visible by the camera 42.

The size of the images taken by the camera 42 is preferably the size of the sock support structure 46 as illustrated in FIG. 5. The area illuminated by the first light 70 is represented by the area defined inside the ellipse 80. The thickness of the collimated light beam of the second light 72 is represented by the space between lines 82,84 in FIG. 4. The height of the collimated light beam is represented by the distance between lines 86,88 in FIG. 5.

The structure 46 of the apparatus of the preferred embodiment further has a pair of parallel wires 90,92 oriented vertically at a known distance from one-another inside the area define by the structure. The pair of parallel wires 90,92, define a longitudinal segment of the collimated light beam. The volume defined between lines 82,84,86,88 and between two vertical transversal planes relative to the collimated light beam, passing through wires 90,92 respectively is a slab of known dimensions. The number of particles observed in this slab, when the second light 72 is lit, can be extrapolated to obtain a representative amount of marine snow in the submarine region being tested.

The operation of both the first and second lights 70,72 is restricted to the time when the camera is recording images, and is preferably of a short duration (less than 2 minutes) so that the mollusks 48 are disturbed as little as possible. The intervals between image sequences being registered by the camera 42 is preferably between about 10 to 30 minutes.

The instrumentation 44 preferably comprises sensors for measuring the conductivity of water, the water temperature and water pressure. The instrumentation also preferably comprises an electronic clock and data storing means for recording the information of the sensors as functions of time, and an electronic compass for recording the alignment of the rudder 37, or the current directions. The instrumentation 44 also preferably contains a time interval programmer and circuitry for operating the first and second lights 70,72 and the camera 42 at random or specified intervals. This feature is particularly advantageous for preventing the mollusks 48 from getting accustomed to the flashes of light and modifying their behaviour accordingly.

When a test is completed in a submarine region and the apparatus 20 of the installation of the first preferred embodiment is pulled out of the water, the data storing means in the form of a disk or a cassette for example, are transferred into a computer for analysis. One example of a software used for analysing images is the image processing system commercialized under the trade name OPTIMAS™. This software is especially useful for obtaining the density, fractal dimension and number of particle per sample of the marine snow visible in the aforesaid light slab of each image.

Other software are also used to interpret and consolidate all the information registered by the apparatus. Pressure readings registered by the instrumentation of the apparatus 20 are used to track the tidal movements. Temperature, salinity, pressure and current records are used to determine the probable origin of the particles being carried through the site. Therefore, the analysis of all the data provides an integrated indication as to whether or not a site will be appropriate for the culture of a specific species of mollusks.

Interpretation of images is effected to determine several behavioural indices which permit to evaluate a normal or stressed condition of one or more mollusk specimens. The Activity Index for example is calculated from observations of shell gape, mantle extension and mantle position. Shell gape position is assigned a number from lowest to highest: closed (0), slit (1), half open (3) or open (5). Mantle state is also assigned a number from lowest to highest: retracted (0), half retracted (3), full (5), and extended (10). Mantle position is recorded as meshed (1) or open (2). The Activity Index is the sum of the values for shell gape, mantle extension and mantle position. The Activity Index is calculated from the average values of as many animals as possible (usually 10–25), given the orientation of mussels in the sock. In addition to the above, the Number Open Index is recorded. The Number Open Index is the percent of mussels that have a mantle position visibly open. The Number Open Index is usually recorded for a much larger number of animals (between 50 and 100). The higher Activity Index with a high Number Open Index indicate healthy conditions, and a lower Activity Index indicate stressful conditions.

Figure 6:
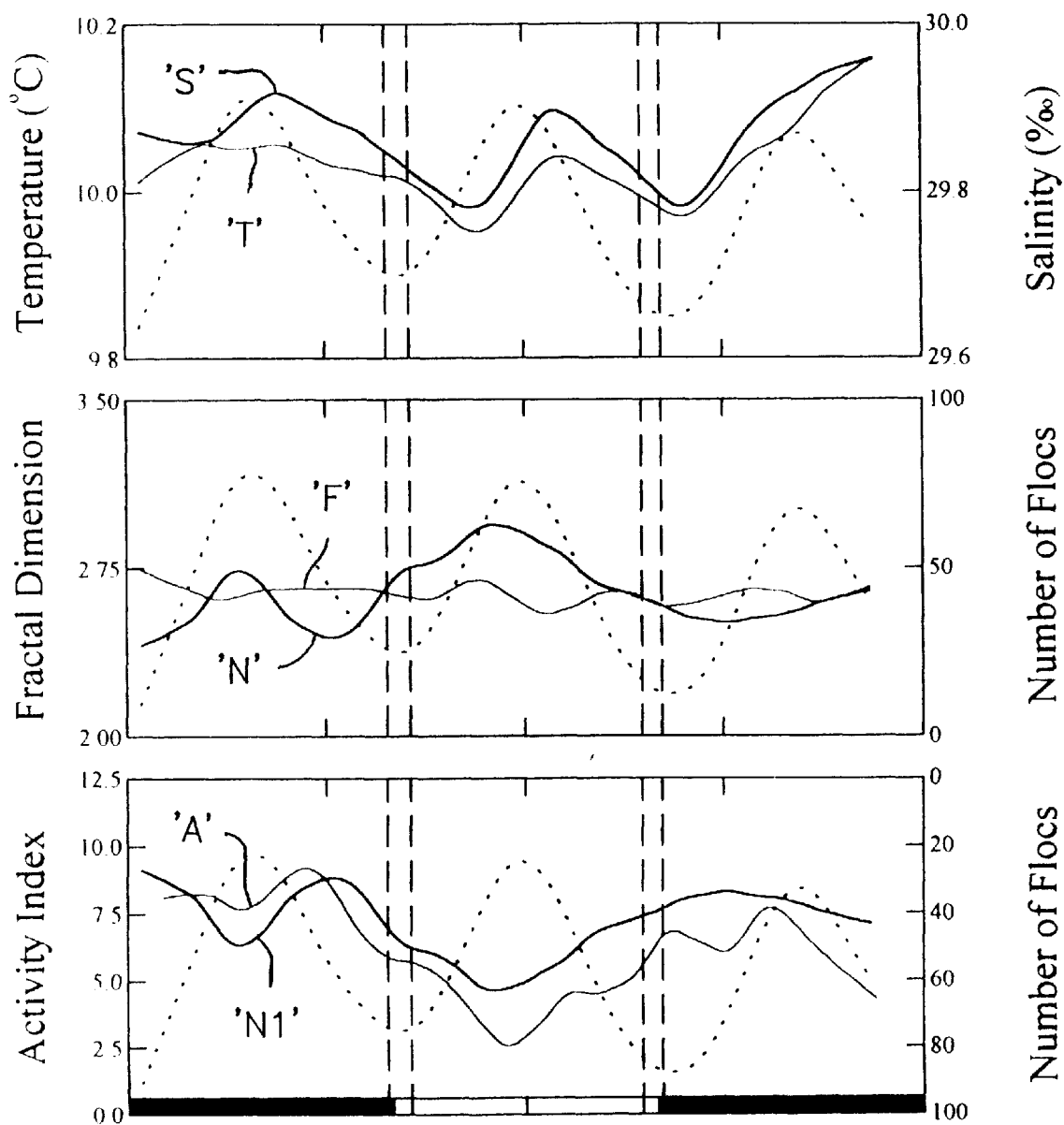
FIG. 6 shows a chart of typical aquatic parameters recorded by the monitoring apparatus of the installation of the first preferred embodiment.

Typical graphs generated from the data registered over a 36-hour period by the apparatus of the installation of the first preferred embodiment are illustrated in FIG. 6. This illustration represents the relation between mussel behaviour, floc dynamics and tidal cycles. Black boxes below each graph indicate periods of darkness. Open boxes indicate times of daylight. Dashed vertical lines show dawn and dusk. Data were plotted against time, and smoothed using LOWESS™, a smoothing algorithm that is useful for observing trends in relationships. Dashed lines in all three graphs indicate water pressure, which describes the tidal cycle.

In the top panel, the 'T' line is temperature, and the 'S' line is salinity. On the second panel, the 'F' line is the fractal dimension of marine snow particles, and the 'N' line is the number marine snow particles in each sample. On the bottom panel, the 'A' line is the Activity Index, and the 'N1' line is again the number of marine snow particles in each sample, shown in a reverse mode for easier visual comprehension. Depth, current, temperature, salinity and local underwater chemistry are stimuli that modify the behaviour of many aquatic organisms, including the feeding behaviour of mollusks. Therefore, the apparatus of the installation of the first preferred embodiment provides hard records of these factors and invertebrate behaviours to enable a better management of marine resources.

The images provided by the apparatus of the installation of the first preferred embodiment are preferably interpreted by scientists in the field marine biology, to determine according to established parameters the behavioural indices of the observed mollusks 48. For example, in order to determine the feeding mode of bivalves, it is necessary to quantify the temporal changes in both the marine snow density and feeding activity of the mollusks. Filtering activity of mollusks can be grossly approximated by valve gape and mantle states as captured on the images registered by the monitoring apparatus.

Another advantage of the monitoring installation of the preferred embodiment is easily deployed by an aquaculture producer for example. The digital or analog data collected by the apparatus are easily transmitted electronically to an interpretation center where marine scientists can prepare and forward back a detailed report of their analyses to the aquaculture producer. This method is highly reliable, quick, easily performed and reasonably inexpensive.

Figure 7:
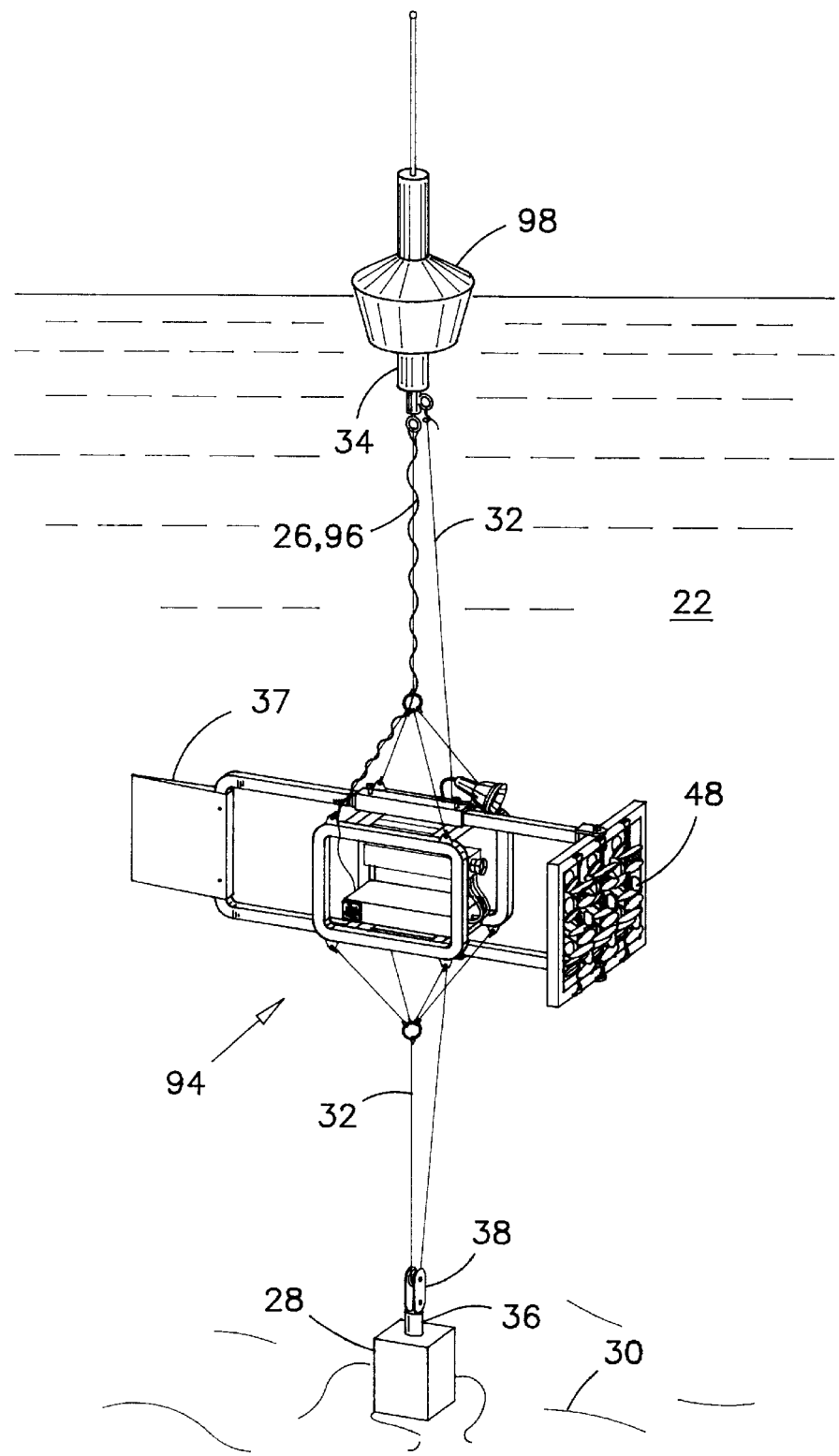
FIG. 7 illustrates an installation of a second preferred embodiment comprising an instrument buoy.
Figure 8:
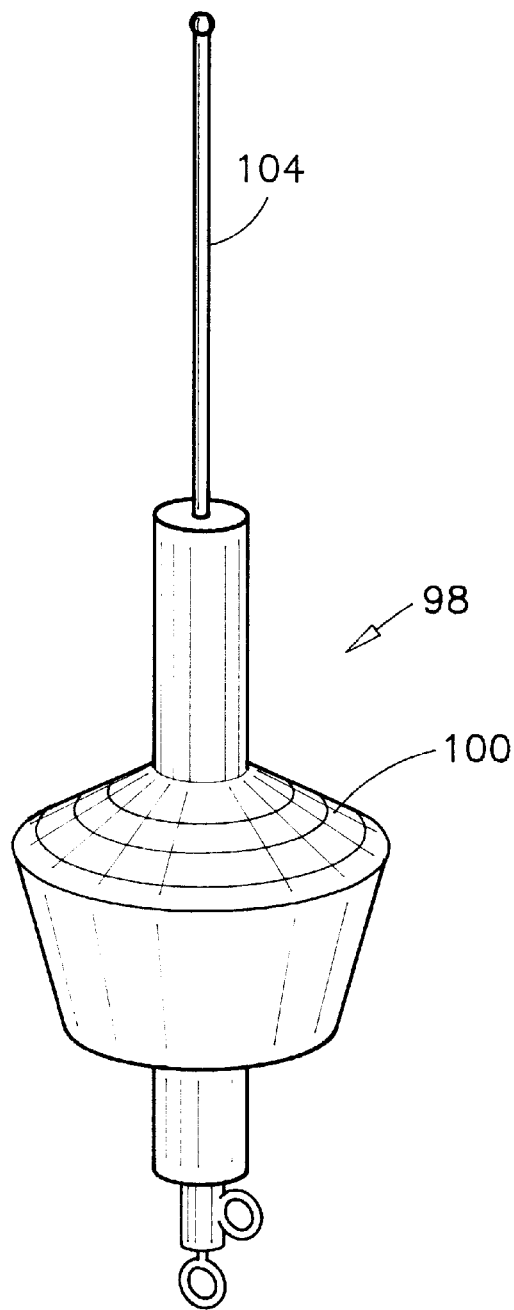
FIG. 8 shows a side view of the instrument buoy used with the installation of the second preferred embodiment.
Figure 9:
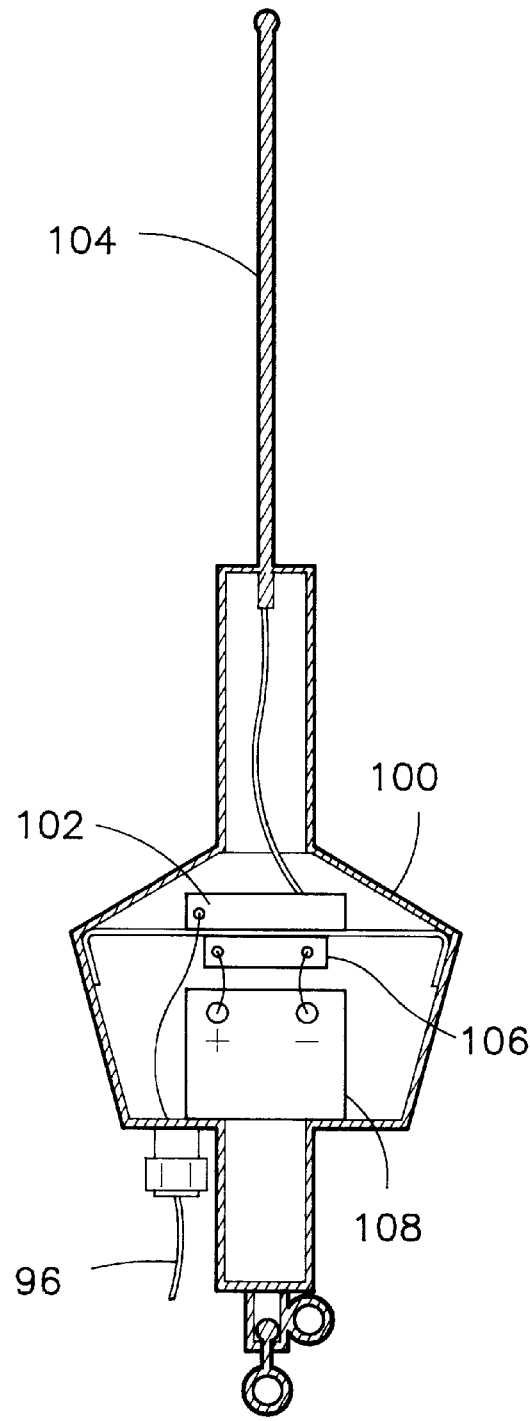
FIG. 9 is a vertical cross-section view of the instrument buoy shown in FIGS. 7 and 8.

It will be appreciated that while the afore-mentioned disclosure is about monitoring installations comprising a self-contained monitoring apparatus where the data are recorded and retrieved at the completion of a test period, the present technology is available to transmit the information on a real time basis to a remote receiver and interpreted using a personal computer. This latter method is preferred for applications where the monitoring installation is used to provide early warning of a pollution problem for example. In this respect, the monitoring apparatus in the installation of the second preferred embodiment 94 is connected by communication cable 96 to an instrument buoy 98 as illustrated in FIGS. 7, 8 and 9.

The preferred instrument buoy 98 is solar powered from a solar panel 100, and contains a data transmitter 102 which receives data from the instrumentation 44 and camera 42 through the communication cable 96 and which transmits the data in a wireless mode through an antenna 104, to a remote receiver. The preferred instrument buoy also contains a battery charger 106 and a battery 108 supplying power to the instruments in the buoy, or to both the instruments in the buoy and the instruments in the monitoring apparatus.

The monitoring apparatus of the installation of the second preferred embodiment 94 can be used with or without the second light 72. When the installation is used as an early warning system especially, the second light 72 is not required, and the support structure 46 is preferably adapted to support a number of socks of mollusks such that the monitoring is carried out with a test sample preferably containing as many as one hundred animals, and in specific cases, a mixture of species or different sizes of individuals.

A continuous status signal travels by cable 96 to the solar-powered instrument buoy 98, from where it is transmitted by wireless communication mode to the operation manager's desktop computer (not shown). There, appropriate visualisation software presents the information from one or more monitoring installation in a format that permits immediate decision-making.

It will be appreciated that the installation of the second preferred embodiment may also be used with the accessories comprised in the monitoring apparatus 20 of the first preferred embodiment, and vice versa.

The monitoring installations of both preferred embodiments comprise portable apparatus, which are relatively inexpensive to manufacture, which can be transported and deployed using a small boat, a skiff or a dory for example. The installations of the preferred embodiments allow the monitoring of aquatic organisms that are at ease with their monitored conditions, such that a variation between a normal and stressed behaviour patterns is as large as possible, and the reliability of each test is high.

While the above description provides a full and complete disclosure of the preferred embodiments of the monitoring installations of the present invention, various modifications and equivalents may be employed without departing from the true spirit and scope of the invention. Such changes might involve alternate structural arrangements, sizes, construction features and the like. Therefore, the above description and the illustrations should not be construed as limiting the scope of the present invention which is defined by the appended claims.

We claim:

1. An apparatus for in situ monitoring a quality of habitat of aquatic organisms, comprising:

a framework having an upper end connectable to a buoy and a lower end connectable to a mooring, a camera attached to said framework, said camera being adapted for underwater operation and having data storage capabilities for registering a number of images;

instrumentation also attached to said framework and containing instruments relative to characteristics of said body of water and a power supply means connected to said instruments for operating said instruments; and a support structure mounted on said framework and extending in front of said camera, said support structure comprising a pair of spaced apart telescopic arms extending away from said camera, and a frame affixed to said telescopic arms, said frame having means for defining a plane perpendicular to a line of sight of said camera, and means for supporting an aquatic organism specimen in front of said camera;

such that said framework is submersible at a set depth in a body of water and a behaviour of an aquatic organism specimen is observable by said camera when said apparatus is adapted to be submerged in said body of water, and said aquatic organism specimen is attached to said support structure.

2. The apparatus as claimed in claim 1, wherein said frame is a rectangular frame.

3. The apparatus as claimed in claim 2, wherein said telescopic arms have clevises, and said clevises have means for pivotally and detachably retaining said rectangular frame to said telescopic arms.

4. The apparatus as claimed in claim 2 wherein said means for supporting an aquatic organism specimen in front of said camera comprises an upper and lower rotary retainers mounted on said rectangular frame for adjustably retaining an aquatic organism specimen to said rectangular frame.

5. An installation for in situ monitoring a quality of habitat of aquatic organisms in a body of water, comprising:

a buoy floating on said body of water;

a mooring resting on a bottom surface of said body of water; and a monitoring apparatus comprising:

a framework being submersed in said body of water, and having an upper end connected to said buoy and a lower end connected to said mooring;

a camera attached to said framework, said camera being adapted for underwater operation and having data storage capabilities for registering a number of images;

instrumentation also attached to said framework, said instrumentation containing instruments relative to characteristics of said body of water and a power supply means connected to said instruments for operating said instruments; and a support structure mounted to said framework and extending in front of said camera, said structure having means for supporting an aquatic organism specimen in front of said camera;

such that a behaviour of an aquatic organism specimen is observable and registrable by said camera for interpretation relative to said quality of habitat.

6. The installation as claimed in claim 5, wherein said means for supporting an aquatic organism specimen in front of said camera comprises means for supporting a sock of mollusks.

7. The installation as claimed in claim 6, wherein said support structure comprises a pair of spaced apart telescopic arms extending away from said camera, and a rectangular frame affixed to said telescopic arms and defining a plane perpendicular to a line of sight of said camera.

8. The installation as claimed in claim 7, wherein said telescopic arms have means for detachably retaining said rectangular frame thereto.

9. The installation as claimed in claim 7 wherein said anchor means comprises an upper and lower rotary retainers mounted on said rectangular frame for adjustably retaining a sock of mollusks in front of said camera.

10. The installation as claimed in claim 9, further comprising a first light for illuminating an aquatic specimens during an operation of said camera.

11. The installation as claimed in claim 5, wherein said monitoring apparatus also comprises a rudder affixed thereto.

12. The installation as claimed in claim 5, further comprising:
  a first light mounted to said framework and oriented to emit light toward said means for supporting an aquatic organism specimen in front of said camera, for lighting an aquatic organism specimen during an operation of said camera; and
  a second light mounted to said support structure and oriented to emit light in a direction perpendicular to a line of sight of said camera during an operation of said camera, for creating reflections on suspended particles near said means for supporting an aquatic organism specimen in front of said camera, and causing said particles to become visible to said camera,
  such that a floc dynamic of a submarine region is observable by said camera together with a behaviour of an aquatic organism specimen exposed to conditions of said submarine region.

13. The installation as claimed in claim 12, wherein said second light has means for emitting a collimated light beam having a nominal height and nominal thickness relative to a sight of said camera.

14. The installation as claimed in claim 13 wherein said rectangular frame further comprises a pair of spaced apart parallel wires attached thereto and being oriented perpendicularly to said beam of light and defining a nominal longitudinal segment of said beam of light relative to said sight of said camera.

15. The installation as claimed in claim 14, wherein said first and second lights have means for emitting red light.

16. The installation as claimed in claim 5, wherein said camera also has means for generating digital images, and said buoy comprises transmitter means mounted therein and being connected to said means for generating digital images, for transmitting digital images of a behaviour of an aquatic organism specimen observed by said camera, to a remote location.

17. The installation as claimed in claim 16, wherein said framework comprises means for detachably supporting said support structure thereto.

18. The installation as claimed in claim 17, wherein said buoy further comprises a solar panel, a battery charger connected to said solar panel, and a battery connected to said battery charger, to said camera and to said transmitter means.

19. A method for defining an activity index representative of a behaviour of mollusks in a body of water; comprising the steps of:
  observing, using a camera, a plurality of mollusk specimens in a body of water;
  observing a shell gape, mantle extension and mantle position of said plurality of mollusk specimens, from an image generated by said camera;
  assigning a shell gape first number to an observed shell gape in a closed position; a shell gape second number, larger than said shell gape first number, to an observed shell gape in a slit position; a shell gape third number, larger than said shell gape second number, to an observed shell gape in a half open position, a shell gape fourth number larger than said shell gape third number, to an observed shell gape in an open position;
  assigning a mantle state first number to an observed mantle in a retracted state; a mantle state second number, larger than said mantle state first number, to an observed mantle in a half retracted state, a mantle state third number, larger than said mantle state second number, to an observed mantle in a full state, and a mantle state fourth number, larger than said mantle state third number, to an observed mantle in an extended state;
  assigning a mantle position first number to an observed meshed mantle position, and a mantle position second number, larger than said mantle position first number, to an observed open mantle position; and
  adding said shell gape first, second, third and fourth numbers; said mantle state first, second, third, fourth numbers; said mantle position first and second numbers to one another for said observed image.

20. The method as claimed in claim 19 wherein said plurality of mollusk specimens comprises between about 10 to about 25 specimens.

* * * * *